(12) United States Patent
Church

(10) Patent No.: US 6,353,145 B1
(45) Date of Patent: Mar. 5, 2002

(54) CHARCOAL POULTICE

(76) Inventor: Glenda Church, 570 N. Ocean Blvd., #12, Pompano Beach, FL (US) 33062

( * ) Notice: Subject to any disclaimer, the term of this patent is extended or adjusted under 35 U.S.C. 154(b) by 0 days.

(21) Appl. No.: 09/405,909

(22) Filed: Sep. 24, 1999

(51) Int. Cl.⁷ .............................................. A61F 13/00
(52) U.S. Cl. .............................. 602/48; 602/41; 602/54
(58) Field of Search ..................................... 602/41–59

(56) References Cited

PUBLICATIONS

Total Health Newsletter Apr. 1999 vol. 2 No. 4 Natural Emergency Therapy: Part 4–Poison Antidotes, Apr. 1999.*

Medicinal Herbs Online, Gangrene, www.egregore.com/disease/gangrene.html, 1966.*

* cited by examiner

*Primary Examiner*—Kim M. Lewis

(57) ABSTRACT

The present invention is a wet or a dry poultice in a porous container, of activated charcoal, and (i) ground psillium husk, or (ii) ground flax seed, alfalfa, and goldenseal. The poultice of the present invention optionally further contains smartweed, and optionally a preservative suitably for the flax seed.

21 Claims, 1 Drawing Sheet

CHARCOAL POULTICE

FIELD OF THE INVENTION

The present invention relates to a charcoal containing poultice for application to part of the body of a host.

BACKGROUND

Charcoal, or wood preserved by charring, or prepared by a distillation of a large number of organic materials or bone, has many known beneficial properties, such as an ability to take up toxic or noxious gases, disease germs, fluid toxic wastes and heavy metals, an adsorbent of toxins in the body, and is thus capable of cleansing and healing the body. The scriptures describe the medicinal use of charcoal compresses, such as in applying fomentations to Hezekiah. Activated charcoal is produced by a controlled burning or charring of the starting material, such as wood or bone, and contact with an oxidizing gas, pressurized steam, or a strong acid, to activate or enhance the adsorptive capacity of charcoal by expanding its specific surface area.

As described e.g. in a book by A. Trash et al., Charcoal, Family Health Publications LLC, 1988, charcoal compresses containing in addition to charcoal and cornstarch or flax seed have been known for application to body surfaces on a fabric pad, such as for the treatment or palliation of animal stings and bites. Hops or smartweed is known to be added to the charcoal material of such compresses and stupes, with fresh or dried leaves added to the charcoal material. These compresses can be applied hot, or a heating pad can be applied over them.

Alfalfa is a natural food supplement,a source of a large variety of minerals and proteins and other nutrients, and it is used to alkalize and detoxify the body, acts as a diuretic, antiinflammatory, blood clotting agent, and is useful in digestive disorders.

Goldenseal, along with other herbals, such as aloe vera, anise, barberry, bilberry, black cohosh, burdock, cat's claw, celery, echinacea, fig, garlic, ginger, ginkgo biloba, hawthorn, horsetail, licorice, milk thistle, nettle, red clover, parsley, pau d' arco, pumpkin, red beet, suma and valerian root, is a natural remedy. Herbs like these are generally used as a herbal extract for internal and external applications of the body, in the form of powders, extracts, tinctures, teas, decoctions, syrups, poultices, salves, infusions, ointments and vinegars. Goldenseal, specifically is known as a medicinally useful herb for internal application as an antibiotic, antiinflammatory, and antibacterial agent which increases the efficiency of insulin, and strengthens the immune system, and other benefits.

U.S. Pat. No. 322,664 discloses a method of producing carbonized vegetable matter -referred to as carbon wool- for an antiseptic dressing.

U.S. Pat No. 2,690,415 relates to an odor adsorbent bandage or dressing for covering odoriferous wounds, corpses and other noxious bodies. The bandage has an adhesive coated web such as of gauze, an odor adsorbent material, such as activated carbon.

A number of other U.S. patents, such as U.S. Pat. Nos. 4,453,929; 4,461,099; 4,711,781; 4,728,642; 4,529,623; 4,657,808; 4,715,857; 4,817,594; 4,822,349; 4,928,681; 5,122,407; and 5,759,943 disclose various medicinal, occlusive, and odor- or -fluid adsorbing charcoal plasters or felts, wound dressings, and the like, which can optionally contain metal powders, fluorocarbons, various medicinal ingredients, such as antihypertensives, antirheumatics, vasodilators, Ca antagonists, β-blockers, antiemetics, antitussives, sedatives, analgesics, antiasthmatics, antiarrhytmics, antihistamines, hormones, antibiotics, cytostatics, and the like.

DESCRIPTION OF THE INVENTION

The present invention is a wet or a dry poultice in a porous container, of activated charcoal, and (i) ground psillium husk, or (ii) ground flax seed, alfalfa, and goldenseal. The poultice of the present invention optionally further contains smartweed, and optionally a preservative suitably for the flax seed.

The poultice of the present invention provides topically relief from and amelioration of various conditions, such as infections such as sinus infections, or skin and body surface infections, suppurations, abscesses, inflammations, stiff or aching joints, and the like.

BRIEF DESCRIPTION OF THE DRAWINGS

The invention is further disclosed by reference to the enclosed drawing, wherein.

DETAILED DESCRIPTION OF AN EMBODIMENT

Figure 1:
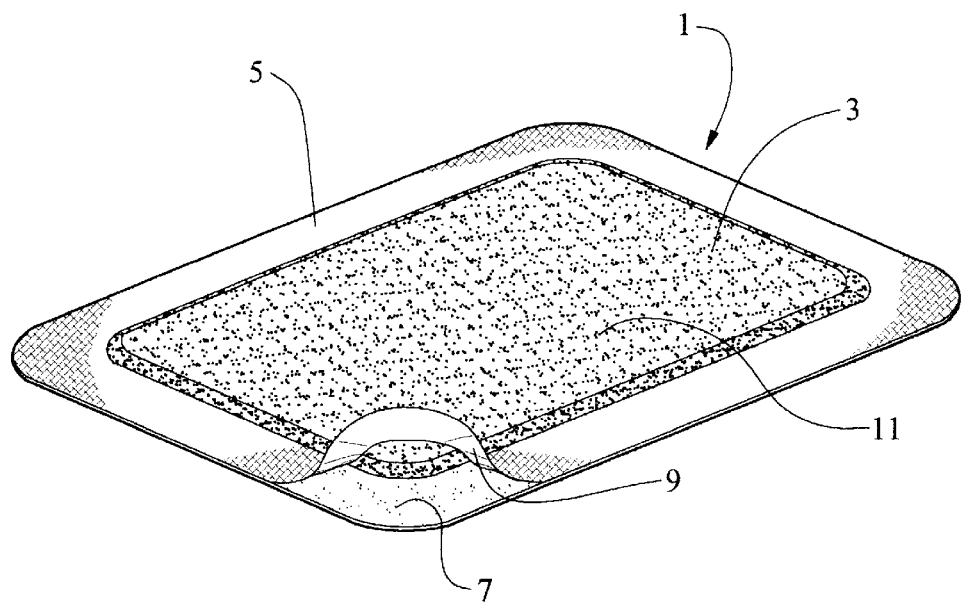
FIG. 1 is a perspective view of a poultice of the invention.
Figure 2:
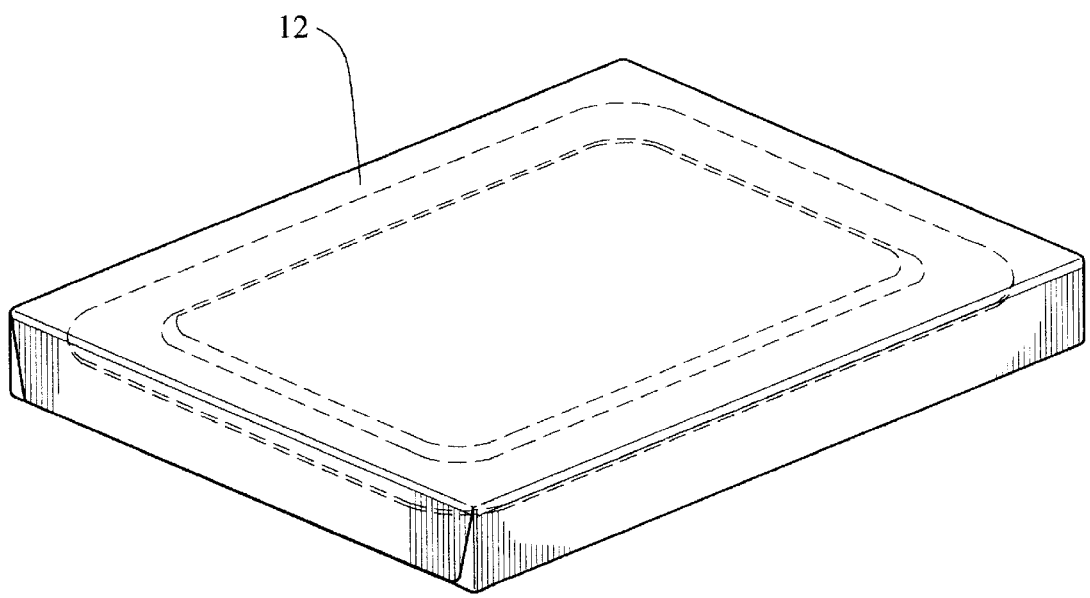
FIG. 2 is a perspective view of a water-impermeable outer packaging for the poultice.

Fig. shows a poultice 1 which in the illustrated embodiment is rectangular, but can be of any desired shape. The envelope of the poultice is a porous container 3, such as of paper, gauze or felt. A periphery 5 of the exterior of the porous container 3, can be provided with an outer adhesive 7 which is either pressure applicable to a skin surface, or can be moisture activated for the same purpose. If the adhesive is of a self-stick type, a peel-away protector strip 9 can be applied over the adjhesive 7, and peeled away before the application of the poultice to a body surface. The poultice can be provided with an outer moisture barrier layer 11 at least on its larger surface which is facing away from the surface to be applied to the body, so that no moisture can escape or run out of the poultice. surface to be applied to the body, so that no moisture can escape or run out of the poultice.

Suitably one or more poltices can be packaged in a water-impermeable outer packaging 12 which can either be a selable envelope, or a lerger water impermeable container for containing and maintaining in wet condition one or more moist poultices of the present invention therein.

The poultice of the present invention suitably contains from about ¼to about 4 cup water, from about 2 to about 10 tablespoons ground flax seed, and from about 2 to about 10 tablespoons of activated charcoal powder, and optionally from about 1 to about 10 tablespoons of smartweed.

The poultice can be suitably prepared from an aqueous mixture of activated charcoal, and (i) psillium husk, or (ii) ground flax seed, alfalfa powder, and goldenseal. The mixture is heated, suitably brought to a boil while stirring. If the mixture contains flax seed, it is cooked until it is thickened or jelled. The mixture is then spread in a layer of a thickness of from about 0.15 inches to about 1 inch onto a substrate, suitably the water-permeable fabric, -paper, or-plastic material of the container.

Suitably one or more poultices can be packaged in a water-impermeable outer packaging 12 which can either be a sealable envelope, or a larger water impermeable container for containing and maintaining in wet condition one or more moist poultices of the present invention therein.

The poultice of the present invention can be packaged moist in a sealed package, or in a container as a plurality of moist poultices or packages, to keep the poultice moist and ready to use. Alternatively the poultice can be packaged dry, and then remoistened, such as by dipping in water before use. Remoistening in warm water can not only be beneficial for some applications, but can also minimize any bleeding through of the contents.

I claim:

1. A poultice which comprises a porous container, and disposed within said container particles of activated charcoal, and ground psillium husk.

2. The poultice of claim 1, wherein said porous container is of a water-permeable fabric, -paper, or -plastic material.

3. The poultice of claim 2, further comprising an adhesive on the periphery of an exterior side of said container for attaching said container to the surface of the body of a host.

4. The poultice of claim 3, wherein said adhesive is a self-stick adhesive.

5. The poultice of claim 4, further comprising a peel-away protector strip for said adhesive.

6. The poultice of claim 2, further comprising smartweed within said container.

7. The poultice of claim 1, further comprising water.

8. The poultice of claim 6, further comprising water.

9. The poultice of claim 7, wherein said container comprises in proportion from about ¼ to about 4 cup water, from about 2 to about 10 tablespoons ground flax seed, and from about 2 to about 10 tablespoons of activated charcoal powder.

10. The poultice of claim 9, further comprising in proportion from about 1 to about 10 tablespoons of smartweed.

11. The poultice of claim 7, wherein one side of said container has a moisture barrier.

12. The poultice of claim 8, wherein one side of said container has a moisture barrier.

13. The poultice of claim 7, further comprising a preservative for said ground flax seed.

14. The poultice of claim 8, further comprising a preservative for said ground flax seed.

15. The poultice of claim 7, further comprising a water-impermeable outer packaging for said poultice.

16. The poultice of claim 8, further comprising a water-impermeable outer packaging for said poultice.

17. A process for preparing a poultice, which comprises preparing an aqueous mixture of activated charcoal, and psillium husk, bringing said mixture to a boil while stirring, spreading said mixture in a layer of a thickness of from about 0.15 inches to about 1 inch onto a water-permeable fabric, -paper, or -plastic material which comprises said container.

18. The process of claim 17, further comprising leaving a margin of from about 0.15 inches to about 1 inch about the edges of said container without having any of the mixture spread in said margin.

19. The process of claim 18, further comprising applying an adhesive to the exterior of said container within said margin.

20. A process for preparing a poultice, comprising the steps of:

providing an aqeous mixture of activated charcoal, psyllium husk and water; and spreading said mixture in a layer onto a container which comprises a water permeable fabric, paper or plastic material.

21. The process for preparing the poultice of claim 20, further comprising the step of boiling said mixture before spreading said mixture onto the container.

* * * * *